(12) United States Patent
Kaisornbundit

(10) Patent No.: US 9,835,534 B2
(45) Date of Patent: Dec. 5, 2017

(54) VOLUMETRIC APPARATUS AND DENSIMETER IN NON LIQUID USAGE TYPE

(71) Applicant: Chaisorn Kaisornbundit, Buriram (TH)

(72) Inventor: Chaisorn Kaisornbundit, Buriram (TH)

( * ) Notice: Subject to any disclaimer, the term of this patent is extended or adjusted under 35 U.S.C. 154(b) by 0 days.

(21) Appl. No.: 15/304,291

(22) PCT Filed: Apr. 27, 2015

(86) PCT No.: PCT/TH2015/000026
§ 371 (c)(1),
(2) Date: Oct. 14, 2016

(87) PCT Pub. No.: WO2015/167406
PCT Pub. Date: Nov. 5, 2015

(65) Prior Publication Data
US 2017/0052099 A1 Feb. 23, 2017

(30) Foreign Application Priority Data

May 1, 2014 (TH) .................. 1401002397

(51) Int. Cl.
*G01N 9/26* (2006.01)
*G01F 17/00* (2006.01)
*G01F 22/02* (2006.01)

(52) U.S. Cl.
CPC .............. *G01N 9/26* (2013.01); *G01F 17/00* (2013.01); *G01F 22/02* (2013.01); *G01N 2009/263* (2013.01)

(58) Field of Classification Search
CPC ........................ G01N 9/26; G01N 2009/263
See application file for complete search history.

(56) References Cited

U.S. PATENT DOCUMENTS

| 3,844,170 A | | 10/1974 | Critten | |
| 4,170,845 A | * | 10/1979 | Owen | E05B 83/02 49/220 |
| 4,766,820 A | * | 8/1988 | Ritter | B61D 7/28 105/240 |

FOREIGN PATENT DOCUMENTS

| CN | 2411464 Y | 12/2000 |
| CN | 101477074 A | 7/2009 |

* cited by examiner

*Primary Examiner* — Jewel V Thompson
(74) *Attorney, Agent, or Firm* — Kenneth E. Horton; Kirton McConkie

(57) ABSTRACT

Volumetric Apparatus and Densimeter in non liquid usage type composes of cylinder which is in shape of tube for filling in by the object needed to be measured with inside pushing support stick for supporting the moving forth-back of pushing stick to transmit the pressure force to make pushing support stick moving forth-back to be able to move forth-back. The moving forth-back of said pushing support stick is to measure the distance of the moving forth-back compared with original distance by send-receive signal transmitter equipped outside cylinder. The cylinder is separated into two parts of which each part supports for in-out pressure by inside pushing stick that push in-pull out by external force to measure the object needed to be measured placed at one part of cylinder that separated to measure the moving forth-back of inside pushing stick by distance meter unit at least two units. Then, the units calculates the changed distances in cylinder as data for finding volume and density and air pressure inside cylinder at least one cylinder and to be sent to pressure and vacuum meter and displays in numbers or signs to show pressure inside cylinder as support data in calculation of volume and density of the object needed to be measured.

20 Claims, 3 Drawing Sheets

VOLUMETRIC APPARATUS AND DENSIMETER IN NON LIQUID USAGE TYPE

TECHNICAL FIELD

Engineering related to volumetric apparatus and densimeter in non liquid usage type

BACKGROUND ARTS

Volumetric apparatus and Densimeter nowadays operates in the way to calculate from geometrical dimension (only matched with object in geometrical shape, for example, rectangular object, for instance), or in the way to fill the desired object in liquid contained in container and measure the replaced liquid with meter.

From the characteristic of volumetric apparatus and densimeter described above, the accuracy of volume and density of measured object is very low, not suitable for bringing the value from measurement to use for the work that needs highly accuracy measurement.

CHARACTERISTIC AND PURPOSE OF THE INVENTION

Volumetric Apparatus and Densimeter in non liquid usage type composes of cylinder which is in shape of tube for filling in by the object needed to be measured with inside pushing support stick for supporting the moving forth-back of pushing stick to transmit the pressure force to make pushing support stick moving forth-back to be able to move forth-back. The moving forth-back of said pushing support stick is to measure the distance of the moving forth-back compared with original distance by send-receive signal transmitter equipped outside cylinder. The cylinder is separated into two parts of which each part supports for in-out pressure by inside pushing stick that push in-pull out by external force to measure the object needed to be measured placed at one part of cylinder that separated to measure the moving forth-back of inside pushing stick by distance meter unit at least two units. Then, the units calculates the changed distances in cylinder as data for finding volume and density and air pressure inside cylinder at least one cylinder and to be sent to pressure and vacuum meter and displays in numbers or signs to show pressure inside cylinder as support data in calculation of volume and density of the object needed to be measured.

The purpose of this invention is to have volumetric apparatus and densimeter in non liquid usage type to measure volume and density of object needed to be measured by said invention.

DISCLOSURE OF INVENTION

Figure 1:
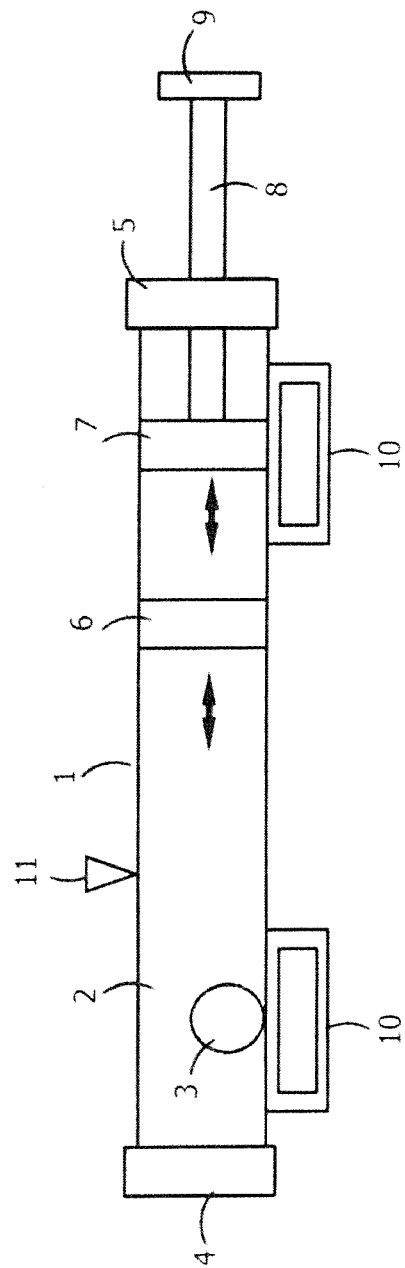
FIG. 1 shows volumetric apparatus and densimeter in non liquid usage type according to this invention.

According to FIG. 1, it shows volumetric apparatus and densimeter in non liquid usage type of this invention, composing of cylinder 1 that is lengthy tube with inside hollow 2 or wall sheet separated each side with inside hollow 2 for being filled with the object needed to be measured 3 which At the left open ended of cylinder 1, there is left door 4 for protecting air or object needed to be measured 3 that filled in inside hollow 2 moving out from left door 4 and At the right open ended of cylinder 1, there is right door 5 for protecting air or object needed to be measured 3 that filled in inside hollow 2 moving out from right door 5 and Another part of inside hollow 2 of cylinder 1, there is pressure axle 6 inserted, which Pressure axle 6 is the stick or thick sheet inserted inside hollow 2 for supporting the pushing in or pulling out from external force and Another part of inside hollow 2 of cylinder 1, there is right pushing axle 7 inserted which Right pushing axle 7 is the axle that moves forth-back and attached with inner end of right pushing stick 8 for supporting pushing out or pulling back from external force to right pushing stick 8, which Right pushing stick 8 is lengthy stick with its inner end inserted through right door 5 for attached with one side of right pushing axle 7 for supporting pushing up or pulling out from pressure sent through outside end of right pushing stick 8, or Outside end of right pushing stick 8 is connected with right holding base 9 which is plate or handle bar for holding and sending pressure to pushing up or pulling out against right pushing stick 8, and At the outside of cylinder 1, there is sending-receiving moving distance unit 10 which is tool or equipment capable for sending-receiving light or sound signal or inducing, placing in distance at least two units and operating by electric voltage from outside. It also installed with display unit or equipment control unit to measuring the distance between original distance and the changing distance of pressure axle 6 and bring the distances data to calculate for volume or density of object needed to be measured 3 that is filled in inside hollow 2 of cylinder 1 and At another part of cylinder 1, there is inside pressure valve 11 at least one unit for control pressure in inside hollow 2 of cylinder 1.

Figure 2:
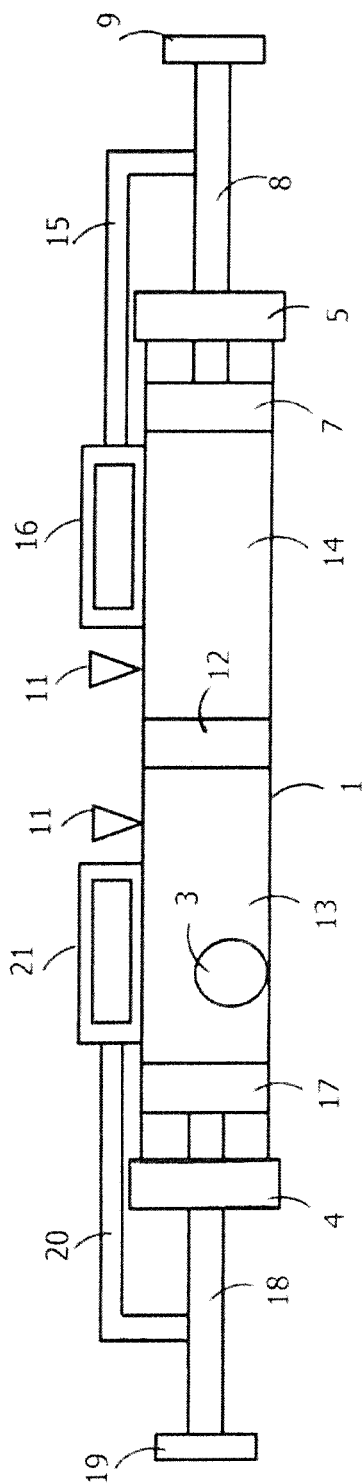
FIG. 2 shows volumetric apparatus and densimeter in non liquid usage type according to this invention in another characteristic.
Figure 3:
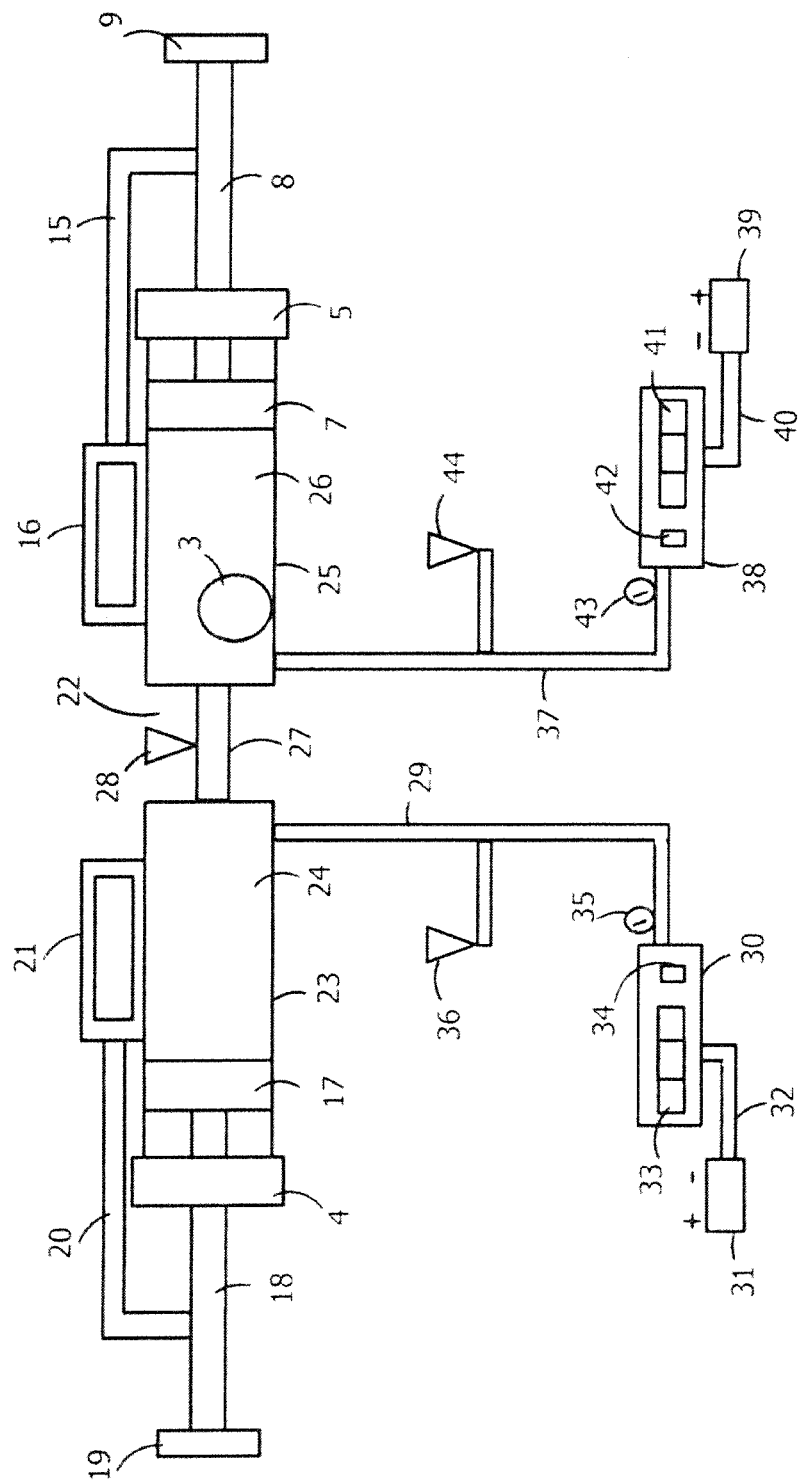
FIG. 3 shows volumetric apparatus and densimeter in non liquid usage type according to this invention in another characteristic.

According to FIG. 2, it shows volumetric apparatus and densimeter in non liquid usage type of this invention in other characteristic composing of cylinder 1 that is tube with inside hollow 2 or wall sheet separated each side with inside hollow 2 for being filled with the object needed to be measured 3 which At the left open ended of cylinder 1, there is left door 4 for protecting air or object needed to be measured 3 that filled in inside hollow 2 moving out from said left door and At the right open ended of cylinder 1, there is right door 5 for protecting air or object needed to be measured 3 that filled in inside hollow 2 moving out from said right door and Another part of inside hollow 2 of cylinder 1, there is inside separated edge 12 with some thickness holding and replacing pressure axle 6 that inserted in inside hollow 2 of cylinder 1, which Inside separated edge 12 is stick or sheet or edge placed inside hollow 2 of cylinder 1 to separate space in inside hollow 2 of cylinder 1 as left inside hollow 13 and right inside hollow 14 and Outside of right pushing stick 8 which located outside cylinder 1 is attached with one end of right forth-back moving stick 15, which Right forth-back moving stick 15 is curved lengthy stick of which its one end stick with outside of right pushing stick 8 outside of cylinder 1 for taking another end attached with right movement measuring unit 16 which Right movement measuring unit 16 is tool or equipment that is installed at the right side of cylinder 1 and operating by electric voltage from outside. It also installed with display unit or equipment control unit to support the installing with one end of right forth-back moving stick 15 to measure the moving forth-back of right forth-back moving stick 15 while right forth-back moving stick 15 received force through the forth-back movement which is the forth-back movement of right pushing stick 8, and In left inside hollow 13 of cylinder 1, there is left pressure axle 17 inserted, which Left pressure axle 17 is axle moved forth-back with inside end of left pressure stick 18 attached for supporting pushing up or pulling out from active force against left pushing stick 18, which Left pushing stick 18 is lengthy stick with its inside end inserted through left door 4 for attached with on side of left pressure axle 17 for supporting pushing up or pulling out from pressure transmitted through outside end of left pushing stick 18, or Outside end of left pressure stick 18, there is left holding base 19 which is plate or handle bar for holding or attached with desired part for sending pressure to pushing up or pulling out of left pushing stick 18, and Outside of left pushing stick 18 which is outside of cylinder 1, there is one end of left forth-back moving stick 20 attached, which Left forth-back moving stick 20 is curved lengthy stick of which its one end stick with outside of left pushing stick 18 outside of cylinder 1 for taking another end attached with left movement measuring unit 21 which Left movement measuring unit 21 is tool or equipment that is installed at the right side of cylinder 1 and operating by electric voltage from outside. It also installed with display unit or equipment control unit to support the installing with one end of left forth-back moving stick 20 to measure the moving forth-back of left forth-back moving stick 20 while left forth-back moving stick 20 received force through the forth-back movement which is the forth-back movement of left pushing stick 18, and Right movement measuring unit 16 measures distance between original distance and changing distance of right pushing stick 8 and left movement measuring unit 21 measures distance between original distance and changing distance of left pushing stick 18. It brings the data from changed distance from right movement measuring unit 16 and changed distance from left movement measuring unit 21 into calculation to find volume or density of object needed to be measured 3 in left inside hollow 13 and right inside hollow 14.

According to FIG. 2, it shows volumetric apparatus and densimeter in non liquid usage type of this invention in other characteristic composing of cylinder 1 which is separated to form hollow between cylinder 22 and categorized into left cylinder 23 with hollow inside left cylinder 24 for being filled with object needed to be measured 3 (not shown in figure) and right cylinder 25 with hollow inside right cylinder 26 for being filled with object needed to be measured 3 which Around hollow between cylinder 22, there is air connecting cylinders tube 27 which is lengthy tube for connecting air between left cylinder 23 and right cylinder 25 to transfer in-out air to each other and Around air connecting cylinder tube 27, there is air control valve 28 at least one valve for control air flow in air connecting cylinder tube 27 and At part of left cylinder 23, there is one end of left pressure tube 29 connected, which Left pressure tube 29 is lengthy tube with one of its end connected with hollow inside left cylinder 24 and another one end connected with the entrance of left pressure and vacuum meter 30 for measure air pressure in environment that is controlled from hollow inside left cylinder 24 and Left pressure and vacuum meter 30 is meter that operated by electric power transmitted from left battery 31 or electric power transmitted from outside source through left electric conductor wire 32 to display result from measuring air pressure in desired environment in hollow inside left cylinder 24 through left display unit 33 and Part of left pressure and vacuum meter 30, there is left control unit 34 which is push button or sway or roll at least one unit installed for control the operation of the invention by the user with non liquid usage type, and Part of left pressure and vacuum meter 30, there is left air pressure control unit 35 which is the unit that could function level of pressure or control level of pressure in-out of left pressure and vacuum meter 30 installed for measuring or control level of pressure in-out of left pressure and vacuum meter 30 and Another part of left pressure tube 29, there is open end that connected with exit of left air pressure out valve 36 for flowing air to inside of left pressure tube 29 and Part of right cylinder 25, there is one open end of right pressure tube 37 connected which Right pressure tube 37 is lengthy tube with one of its end connected with hollow inside right cylinder 26 and another one end connected with the entrance of right pressure and vacuum meter 38 for measure air pressure in environment that is controlled from hollow inside right cylinder 26 and Right pressure and vacuum meter 38 is meter that operated by electric power transmitted from right battery 39 or electric power transmitted from outside source through right electric conductor wire 40 to display result from measuring air pressure in desired environment in hollow inside right cylinder 26 through right display unit 41 and Part of right pressure and vacuum meter 38, there is right control unit 42 which is push button or sway or roll at least one unit installed for control the operation of the invention by the user with non liquid usage type, and Part of right pressure and vacuum meter 38, there is right air pressure control unit 43 which is the unit that could function level of pressure or control level of pressure in-out of right pressure and vacuum meter 38 installed for measuring or control level of pressure in-out of right pressure and vacuum meter 38 and Another part of right pressure tube 37, there is open end that connected with exit of right air pressure out valve 44 for flowing air to inside of right pressure tube 37 and Left pressure and vacuum meter 30 measures air pressure inside hollow inside left cylinder 24 in desired environment to know the changed result. Right pressure and vacuum meter 38 measures air pressure inside hollow inside right cylinder 26 in desired environment to know the changed result as the same. Then, it brings the result to calculate to find volume or density of object needed to be measure 3 while it is filled within hollow inside left cylinder 24 or hollow inside right cylinder 26.

Best Mode for Carrying out the Invention

As the same as mention in Disclosure of Invention

The invention claimed is:

1. A volumetric apparatus and densimeter, comprising:
a non-liquid usage type cylinder containing a lengthy tube with a hollow inside and a wall sheet on each side of the hollow inside, wherein one end of the cylinder is a left door and another end of the cylinder is a right door, wherein the right door supports a right pushing axle which moves from an external force from a right pushing stick, wherein the right pushing stick comprises a lengthy stick with an inner end inserted through the right door of the cylinder and is attached to one side of the right pushing axle and the other end of the right pushing stick is connected to a right holding base;
wherein the hollow inside of the cylinder is supported to be filled in with an object needed to be measured and contains a pressure axle which moves back and forth from the pressure exerted by the right pushing axle; and
wherein the outside of the cylinder contains a control unit comprising a tool capable of sending and receiving a light, a sound signal, or an induced external electric voltage, the control unit measuring the distance between an original distance and a changed distance of the pressure axle within the cylinder and sending distance data to calculate the volume or density of object needed to be measured located within the cylinder.

2. The volumetric apparatus and densimeter of claim 1, further comprising an inside pressure valve for a pressure control unit located in the hollow inside of cylinder.

3. The volumetric apparatus and densimeter of claim 1, the cylinder further comprising an internal separator with a thickness for holding and replacing the pressure axle, the internal separator separating said hollow inside into a left hollow and a right hollow.

4. The volumetric apparatus and densimeter of claim 1, wherein a right pushing stick is located outside the cylinder and is attached to one end of a right moving stick, the right moving stick comprising curved lengthy stick with one end attached to a right measuring unit, wherein the right measuring unit is installed on the right side of the cylinder and operated by external electric voltage, wherein the right measuring unit measures the movement of the right moving stick when it receives force through the movement of the right pushing stick.

5. The volumetric apparatus and densimeter of claim 3, wherein a left pressure axle is located in the left hollow of the cylinder and is connected to one end of a left pushing stick, wherein the left pushing stick is located outside the cylinder and is attached to one end of a left moving stick, the left moving stick comprising curved lengthy stick with one end attached to a left measuring unit.

6. The volumetric apparatus and densimeter of claim 5, wherein the left measuring unit is installed on the left side of the cylinder and operated by external electric voltage, wherein the left measuring unit measures the movement of the left moving stick when it receives force through the movement of the left pushing stick.

7. The volumetric apparatus and densimeter of claim 6, wherein a left holding base is located on outside end of the left pressure stick and comprises a plate or handle bar for holding part of the left pushing stick.

8. The volumetric apparatus and densimeter of claim 1, wherein the cylinder is separated to into a left cylinder with left hollow and a right cylinder with a right hollow with an air connection tube for connecting the left cylinder and the right cylinder.

9. The volumetric apparatus and densimeter of claim 8, further comprising an air control valve for controlling air flow in the air connection tube.

10. The volumetric apparatus and densimeter of claim 9, wherein one end of a left pressure tube is connected to the left cylinder and the other end connected to a left pressure and vacuum meter which operated by electric power transmitted from a left battery or from an outside source through a left electric conductor wire to display results of measuring air pressure in the left hollow of the left cylinder.

11. The volumetric apparatus and densimeter of claim 10, wherein part of left pressure tube contains an open end that is connected with the exit of left air pressure valve that controls the air flowing to the inside of the left pressure tube.

12. The volumetric apparatus and densimeter of claim 8, wherein one end of a right pressure tube is connected to the right cylinder and the other end connected to a right pressure and vacuum meter which operated by electric power transmitted from a right battery or from an outside source through a right electric conductor wire to display results of measuring air pressure in the right hollow of the right cylinder.

13. The volumetric apparatus and densimeter of claim 12, wherein part of right pressure tube contains an open end that is connected with the exit of right air pressure valve that controls the air flowing to the inside of the right pressure tube.

14. A volumetric and densimeter apparatus, comprising:
a cylinder containing a hollow tube, wherein one end of the cylinder is a left door and another end of the cylinder is a right door, wherein the right door supports a right pushing axle which moves from an external force from a right pushing stick having an inner end inserted through the right door of the cylinder and attached to one side of the right pushing axle and the other end of the right pushing stick connected to a right holding base;
wherein the cylinder is configured to be filled in with an object needed to be measured and contains a pressure axle which moves back and forth from the pressure exerted by the right pushing axle; and
wherein the outside of the cylinder contains a control unit comprising a tool capable of sending and receiving a light, a sound signal, or an induced external electric voltage, the control unit measuring the distance between an original distance and a changed distance of the pressure axle within the cylinder and sending distance data to calculate the volume or density of object needed to be measured located within the cylinder.

15. The apparatus of claim 14, further comprising an inside pressure valve for a pressure control unit located in the hollow inside of cylinder.

16. The apparatus of claim 14, wherein a right pushing stick is located outside the cylinder and is attached to one end of a right moving stick, the right moving stick having one end attached to a right measuring unit, wherein the right measuring unit is installed on the right side of the cylinder and operated by external electric voltage and the right measuring unit measures the movement of the right moving stick when it receives force through the movement of the right pushing stick.

17. The apparatus of claim 14, wherein a left pressure axle is located in a left portion of the cylinder and is connected to one end of a left pushing stick, wherein the left pushing stick is located outside the cylinder and is attached to one end of a left moving stick, the left moving stick having one end attached to a left measuring unit.

18. The apparatus of claim 17, wherein the left measuring unit is installed on the left side of the cylinder and operated by external electric voltage, wherein the left measuring unit measures the movement of the left moving stick when it receives force through the movement of the left pushing stick.

19. The apparatus of claim 18, wherein a left holding base is located on an outside end of the left pressure stick and comprises a plate or handle bar for holding part of the left pushing stick.

20. The apparatus of claim 14, wherein the cylinder is separated to into a left cylinder with left hollow and a right cylinder with a right hollow with an air connection tube for connecting the left cylinder and the right cylinder and an air control valve for controlling air flow in the air connection tube.

\* \* \* \* \*